United States Patent
La Lumondiere et al.

(10) Patent No.: US 8,212,215 B2
(45) Date of Patent: Jul. 3, 2012

(54) REFRACTION ASSISTED ILLUMINATION FOR IMAGING

(75) Inventors: Stephen La Lumondiere, Torrance, CA (US); Terence Yeoh, Pasadena, CA (US)

(73) Assignee: The Aerospace Corporation, El Segundo, CA (US)

( * ) Notice: Subject to any disclaimer, the term of this patent is extended or adjusted under 35 U.S.C. 154(b) by 0 days.

(21) Appl. No.: 13/368,026

(22) Filed: Feb. 7, 2012

(65) Prior Publication Data
US 2012/0135550 A1    May 31, 2012

Related U.S. Application Data

(63) Continuation of application No. 12/590,262, filed on Nov. 5, 2009, now Pat. No. 8,138,476.

(51) Int. Cl.
*G01J 5/02* (2006.01)
(52) U.S. Cl. .................................. 250/339.11
(58) Field of Classification Search .. 250/339.1–339.11, 250/339.12, 339.13, 339.14, 339.15
See application file for complete search history.

(56) References Cited

U.S. PATENT DOCUMENTS

| | | | |
|---|---|---|---|
| 5,131,963 A | 7/1992 | Ravi | |
| 5,192,980 A * | 3/1993 | Dixon et al. | 356/326 |
| 5,196,716 A | 3/1993 | Moriya et al. | |
| 5,220,403 A * | 6/1993 | Batchelder et al. | 356/450 |
| 5,754,514 A * | 5/1998 | Guerra | 369/116 |
| 5,757,050 A | 5/1998 | Adler et al. | |
| 5,930,588 A | 7/1999 | Paniccia | |
| 5,946,543 A | 8/1999 | Kimura et al. | |
| 6,005,965 A | 12/1999 | Tsuda et al. | |
| 6,055,055 A | 4/2000 | Toh | |
| 6,266,130 B1 * | 7/2001 | Hasegawa et al. | 355/53 |
| 6,734,960 B1 | 5/2004 | Goto et al. | |
| 6,859,516 B2 | 2/2005 | Schneider et al. | |
| 6,906,801 B2 * | 6/2005 | Borden et al. | 356/432 |
| 2002/0005493 A1 | 1/2002 | Reese et al. | |
| 2002/0180965 A1 | 12/2002 | Engelhardt et al. | |
| 2004/0119018 A1 | 6/2004 | Alfano et al. | |
| 2005/0001900 A1 | 1/2005 | Kreh et al. | |
| 2005/0231713 A1 | 10/2005 | Owen et al. | |

(Continued)

FOREIGN PATENT DOCUMENTS

EP    0887621 A1    12/1998

(Continued)

OTHER PUBLICATIONS

International Search Report and Written Opinion of the International Search Authority mailed in Application No. PCT/US2010/046978 on Dec. 17, 2010.

(Continued)

*Primary Examiner* — Kiho Kim
(74) *Attorney, Agent, or Firm* — K & L Gates LLP (57) ABSTRACT

Various embodiments are directed to systems and methods of imaging subsurface features of objects. An illumination source may be directed towards a surface of an object comprising subsurface features at a first angle relative to the normal of the surface. The object may have a portion between the subsurface features and the surface that has an index of refraction that is greater than the index of refraction of a surrounding medium. An imaging device may be placed with an objective lens oriented substantially normal to the surface. The first angle may be larger than an acceptance angle of the objective lens.

17 Claims, 8 Drawing Sheets

U.S. PATENT DOCUMENTS

| | | |
|---|---|---|
| 2005/0245005 A1 | 11/2005 | Benson |
| 2007/0031995 A1 | 2/2007 | Kaneko |
| 2008/0240548 A1 | 10/2008 | Yeoh et al. |
| 2009/0002688 A1 | 1/2009 | Soeda et al. |
| 2009/0045415 A1 | 2/2009 | Koshiba |
| 2009/0066933 A1 | 3/2009 | Takano et al. |
| 2011/0102615 A1 | 5/2011 | La Lumondiere et al. |
| 2011/0102770 A1 | 5/2011 | La Lumondiere et al. |
| 2012/0019707 A1 | 1/2012 | La Lumondiere et al. |

FOREIGN PATENT DOCUMENTS

| | | |
|---|---|---|
| WO | WO 98/21687 A1 | 5/1998 |
| WO | WO 2008/119550 A1 | 10/2008 |
| WO | WO 2008/120883 A1 | 10/2008 |

OTHER PUBLICATIONS

International Search Report and Written Opinion of the International Search Authority mailed in Application No. PCT/US2011/028514 on Jun. 24, 2011.

Vasefi et al., "An Optical Imaging Technique Using Deep Illumination in the Angular Domain," 2007, IEEE Journal of Selected Topics in Quantum Electronics, vol. 13, No. 6, pp. 1610-1620.

Non-Final Office Action mailed Nov. 26, 2010 in U.S. Appl. No. 12/590,262.

Final Office Action mailed Mar. 24, 2011 in U.S. Appl. No. 12/590,262.

Non-Final Office Action mailed Jul. 27, 2011 in U.S. Appl. No. 12/590,262.

Notice of Allowance mailed Nov. 14, 2011 in U.S. Appl. No. 12/590,262.

* cited by examiner

REFRACTION ASSISTED ILLUMINATION FOR IMAGING

PRIORITY CLAIM

This application is a continuation of co-pending U.S. application Ser. No. 12/590,262 filed on Nov. 5, 2009, which is incorporated herein by reference in its entirety.

BACKGROUND

In semiconductor fabrication and other fields, it is often necessary or desirable to image subsurface objects. For example, when a semiconductor chip is constructed according to "flip-chip" mounting techniques, component structures on the chip are obscured by the substrate. Various semiconductor fabrication and testing techniques require high-contrast imaging of components. Some examples of these techniques include Laser Assisted Chemical Etching, Focused Ion Beam, and others. Imaging through common substrate materials, such as silicon, is possible, although, difficulties exist.

One method of imaging through substrate material is conventional bright field microscopy. According to bright field microscopy, illumination is provided in a direction normal to the substrate surface. An image is captured with a camera or other imaging device also oriented normal to the substrate surface. While this technique can be relatively inexpensive, the resolution of the resulting images is often disappointing. This is, at least in part, because backscatter off of the substrate is directed back towards, and captured by, the objective lens of the imaging device. This has the effect of blurring and washing out the resulting image. It is known to enhance the resolution of bright field microscopy by applying an anti-reflective coating to the substrate. This method, however, is expensive and requires that the target semiconductor chip be subjected to one or more additional processing steps. It is also known to use laser scanning confocal microscopy to achieve higher resolution images through semiconductor substrates. Although laser scanning confocal microscopy does produce good results, the equipment for implementing it is extremely expensive, limiting its practical usefulness.

SUMMARY

In one general aspect, embodiments of the present invention are directed to systems and methods of imaging subsurface features of objects such as, for example, semiconductor devices. An illumination source may be directed towards a surface of an object comprising subsurface features, wherein the illumination from the source is directed at a first angle relative to the normal of the surface. The object may have a portion between the subsurface features and the surface, the portion having an index of refraction that is greater than the index of refraction of a surrounding medium that surrounds the object. An imaging device may be placed with an objective lens oriented substantially normal to the surface. The first angle may be larger than an acceptance angle of the objective lens.

FIGURES

Various embodiments of the present invention are described here by way of example in conjunction with the following figures, wherein:

FIG. 7 illustrates one embodiment of the object of FIG. 1 showing two subsurface features and the ray reflections there from.

DESCRIPTION

Various embodiments are directed to systems and methods for imaging subsurface features including, for example, semiconductor components viewed through the backside of a substrate (e.g., "backside imaging"). An illumination source may be side-addressed, or oriented at an angle relative to the normal of the surface to be imaged. An imaging device comprising an objective lens or objective may be positioned with a field of view directed substantially normal to the surface. The side-addressed position of the illumination source may provide increased image resolution in at least two ways. First, specular reflection or back-scatter off of the surface may be directed substantially outside of the acceptance angle of the objective lens. Second, when the surface over the features to be imaged has a relatively high index of refraction, refraction at the interface between the surface and the surrounding medium (e.g., air) may create a spatial filtering effect that further enhances the captured image.

Figure 1:
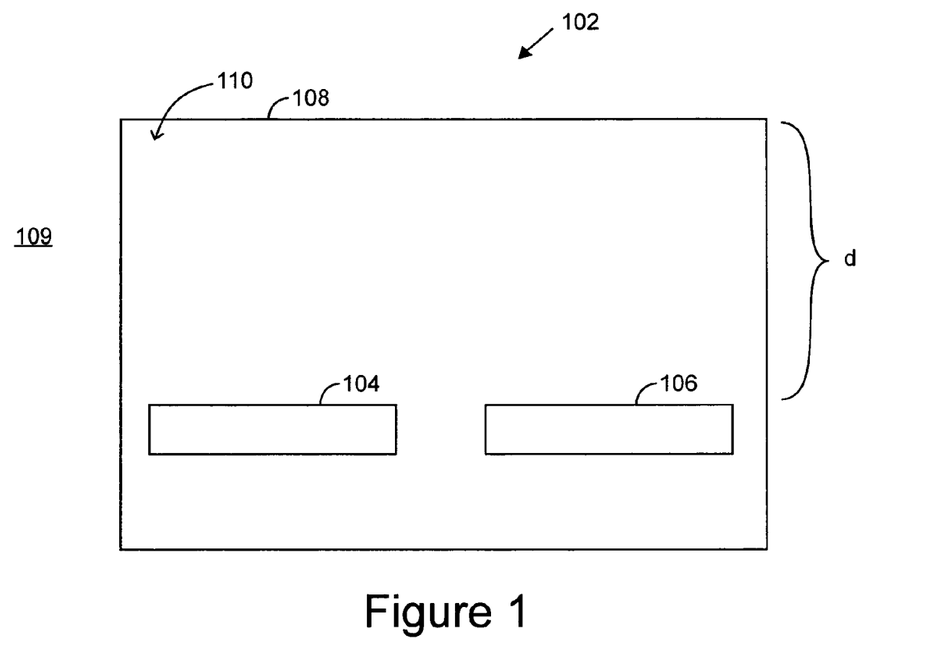
FIG. 1 illustrates a cross-sectional view of one embodiment of an object having subsurface features that may be imaged utilizing the side-addressed illumination techniques described herein.

FIG. 1 illustrates a cross-sectional view of one embodiment of an object 102 having an outer surface 108 and subsurface features 104, 106 that may be imaged utilizing the side-addressed illumination techniques described herein. The material 110 of the object 102 between the subsurface features 104, 106 and the surface 108 may have an index of refraction at the imaging wavelength range that is greater than that of the surrounding medium 109, which may be air. The techniques and apparatuses described herein may be used to image subsurface features in many contexts. In various embodiments, however, the object 102 may comprise a semiconductor substrate and the features 104, 106 may be components such as transistors, diodes, resistors, metallization lines and/or other components formed from or on the substrate of the object 102. In this case, the imaging wavelength range may comprise some or all of the near infrared range, which is transparent in silicon. The ratio of the indices of refraction of the material 110 over the surrounding medium 109 (e.g. air) may be approximately 3.5.

It will be appreciated that, when the object 102 is a semiconductor device, the material 110 may be any suitable semiconductor material including, for example, silicon, gallium arsenide (GaAs), silicon carbide (SiC), and/or diamond. In some embodiments, the object 102 may be mounted in a flip-chip manner. Accordingly, the features 104, 106 may be visible through the remainder of the object 102 (e.g., the substrate). As viewed through the material 110, the features 104, 106 may be below the surface of the object 102 by any suitable distance d that permits transmission of illumination from an illumination source and reformation of an image by the objective or the objective lens of an imaging device (see FIG. 2). In some embodiments, the distance d may be 700 microns.

Figure 2:
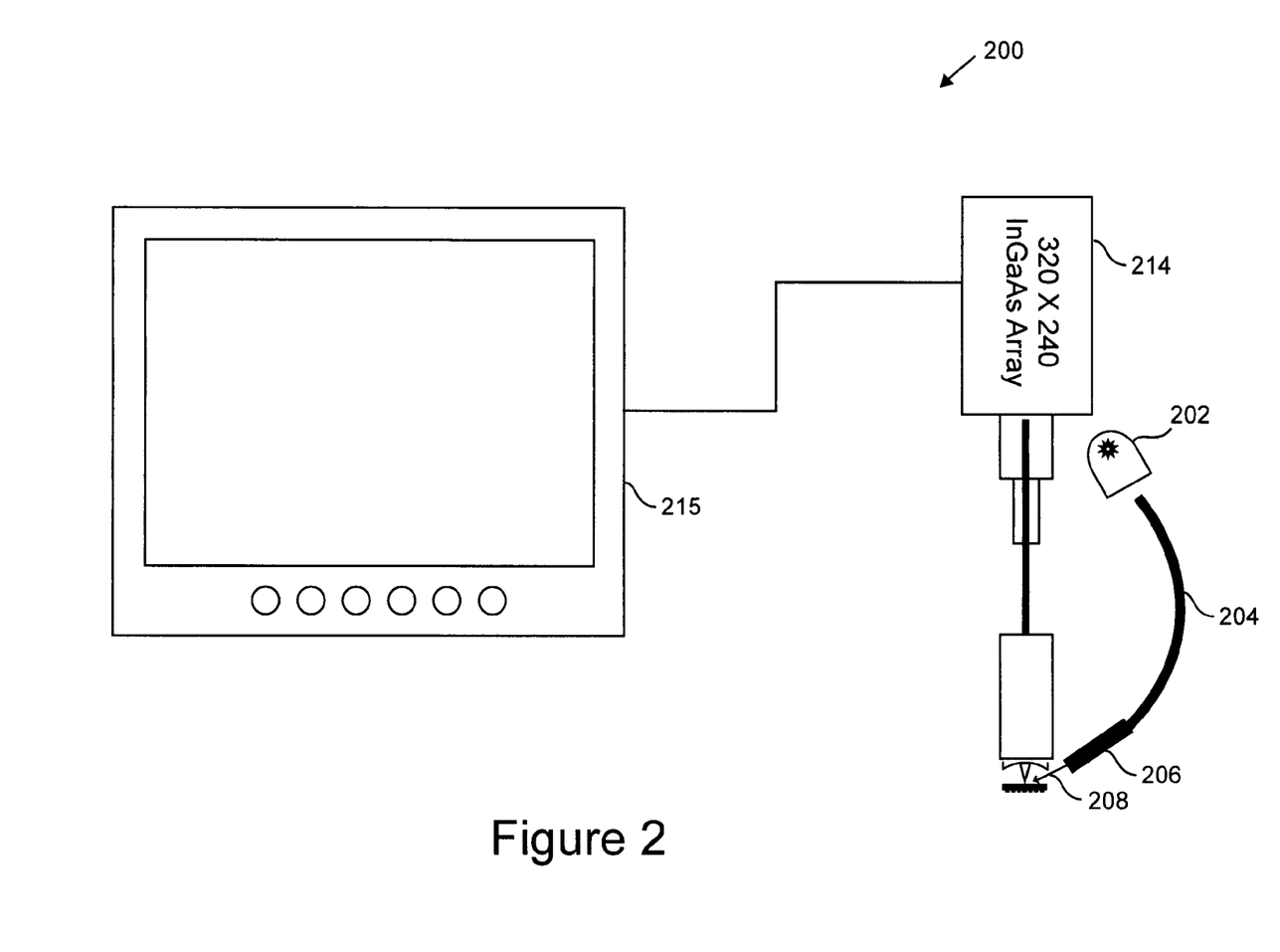
FIG. 2 illustrates one embodiment of a system for side-addressed imaging.

FIG. 2 illustrates one embodiment of a system 200 for side-addressed imaging. The system 200 includes an illumination source 202 optically coupled to a fiber optic bundle 204 (e.g., made of quartz or other suitable material) and a collimating lens 206. According to various embodiments, the source 202 may comprise a tungsten halogen lamp with a gold-plated reflector. It will be appreciated that suitable systems may omit various components such as the fiber optic bundle 204 and collimating lens and/or incorporate some or all of these components into the illumination source 202 itself. Light emitted by the source 202 may be incident on, and may traverse, the fiber optic bundle 204 and collimating lens 206 resulting in a beam 208 incident on the object 102 at an angle offset from the surface normal. Although the source 202 is illustrated as emitting a collimated beam, it will be appreciated that an uncollimated source may be used as well. An objective lens or objective 212 may be positioned approximately along a normal of the object 102 and may direct reflected portions of the beam 208 towards an imaging device 214. The objective 212 may comprise a lens or combination of lenses. The lens or lenses of the objective 212 may comprise a standard lens or, in various embodiments, may comprise a confocal lens for generating three dimensional images. The imaging device 214 may comprise any suitable camera or other imaging element capable of sensing the imaging wavelength range. For example, as shown, the imaging device 214 may comprise a 320×240 Indium Gallium Arsenide (InGaAs) array. The imaging device 214 may capture an image and display it on a monitor 215 or similar visual display device. In addition to, or instead of, displaying the image on the monitor 215, the imaging device 214 may store captured images at a computer readable medium (not shown), such as read only memory (ROM), random access memory (RAM), a hard drive, a flash drive or other data storage device.

According to various embodiments the system 200 may utilize an imaging wavelength or wavelength range that is transparent, or near-transparent, relative to the material 110. For example, when backside imaging is performed through a silicon substrate, the imaging wavelength range may be selected to include wavelengths greater than about 1100 nm. The imaging wavelength range may be implemented in any suitable way. For example, the source 202 may be a broadband source and one or more optical filters may be positioned in the optical path between the source 202 and the imaging device 214. Also, for example, the source 202 may be a narrow-band source that emits only radiation in the imaging wavelength range. In addition to, or instead of these variations, the imaging device 214 may be a narrow band device that is sensitive only to radiation in the imaging wavelength range (e.g., an InGaAs imaging device 214 may be selected with a sensitivity between 900 nm and 1700 nm). In some embodiments, the object 102 may serve as an optical filter. For example, when the object 102 is a silicon substrate and the illumination source 202 is a broadband source, the silicon substrate may tend to absorb all wavelengths other than the near-infrared wavelengths, which are reflected and refracted as described herein.

Figure 3:
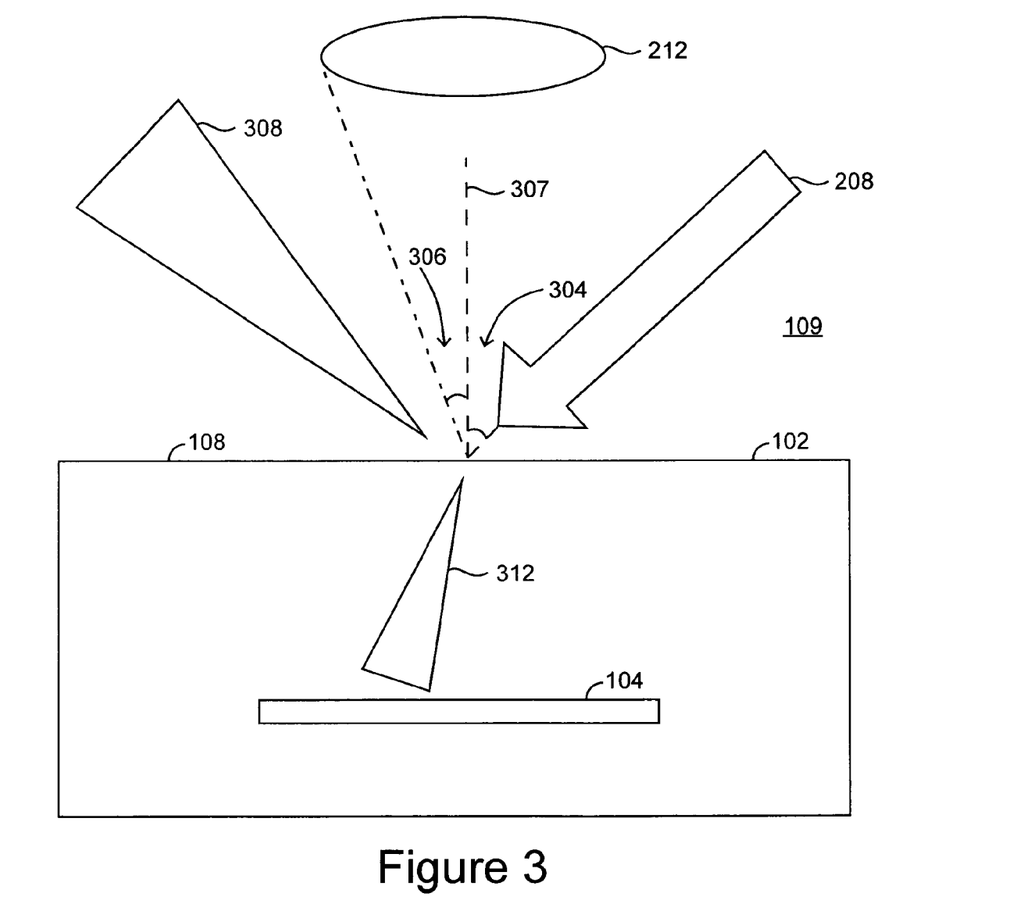
FIG. 3 illustrates one embodiment of the object of FIG. 1 illuminated by an illumination beam.

FIG. 3 illustrates one embodiment of the object 102 showing subsurface feature 104. The incident beam 208 is incident on the object 102 at an angle 304 relative to the surface normal 307. The angle 304 may be set based on the position and orientation of the illumination source 202. The angle 304 may be selected such that specular reflection of the beam 208 off of the object 102 falls outside of an acceptance angle of the objective 212. For example, the angle 304 may be at least equal to the acceptance angle 306 of the objective 212 and less than 90°. It will be appreciated that as the angle 304 increases, the intensity of the light source 202 may also need to be increased to compensate for increasing portions of the illumination beam 208 being reflected off of the object 102 out of the view of the objective 212.

In practice, reflection from the object 102 may not be perfectly specular (e.g., the surface 108 may not be perfectly smooth). Accordingly, the beam 208 may scatter off of the object 102 at a range of angles represented by cone 308. To compensate for this effect, the angle 304 may be selected to be slightly larger than the acceptance angle of the objective 212 such that the actual reflection of the beam 208 off of the object 102 falls substantially outside of the acceptance angle 306 of the objective 212. In this way, the image noise due to surface reflection may be minimized. In one example embodiment where the object 102 is a silicon substrate, the angle 304 may be 45°.

A portion of the beam 208 may be transmitted through the interface between the surrounding medium 109 (e.g., air) and the object 102. Due to the differing indices of refraction between the surrounding medium 109 and the material 110, the resulting light will be refracted towards the normal direction. Also, because the surface 108 of the object 102 may not be perfectly smooth, the refracted portion of the beam 208 may begin to spread, as represented by cone 312. The refracted portion 312 may be incident on and illuminate the feature 104 for imaging.

Figure 4:
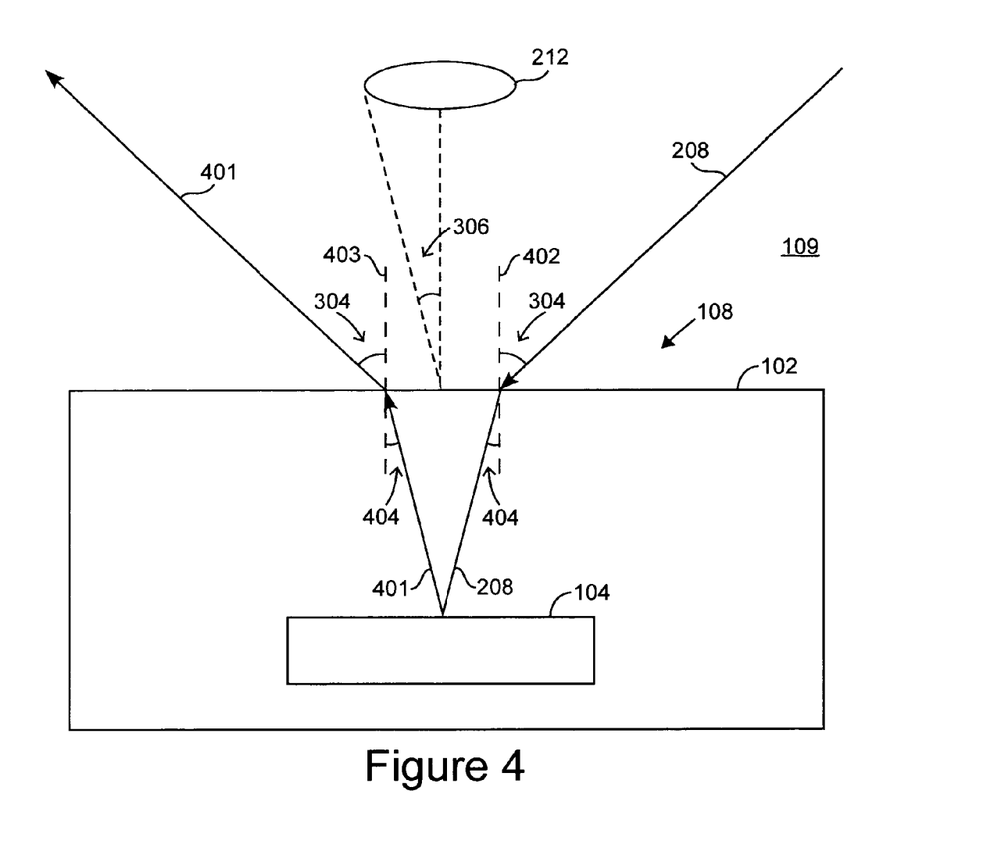
FIG. 4 illustrates one embodiment of the object of FIG. 1 illuminated by the beam oriented at an angle relative to normal of the surface of the object.

FIG. 4 illustrates one embodiment of the object 102 illuminated by the beam 208 oriented at the angle 304 relative to normal of the surface of the object 102 (represented by normal dashed lines 402, 403). At the interface between the object 102 and the surrounding medium 109, the beam 208 may be refracted such that its angle relative to the normal 402 is shown by 404. When the surrounding medium 109 is air (index of refraction ~1), the object 102 is a silicon substrate (index of refraction ~3.5) and the angle 304 is about 45°, given Snell's law, the angle 404 may be about 11.6°. After entering the object 102, the incident beam 208 may reflect off of the feature 104, resulting in a reflected beam 401. The reflected beam 401 may be incident on the surface 108 between the object 102 and the surrounding medium 109 at the angle 404 relative to the normal 403. At the surface 108, the reflected beam 401 may be refracted to the angle 304 relative to the normal 403.

Figure 5:
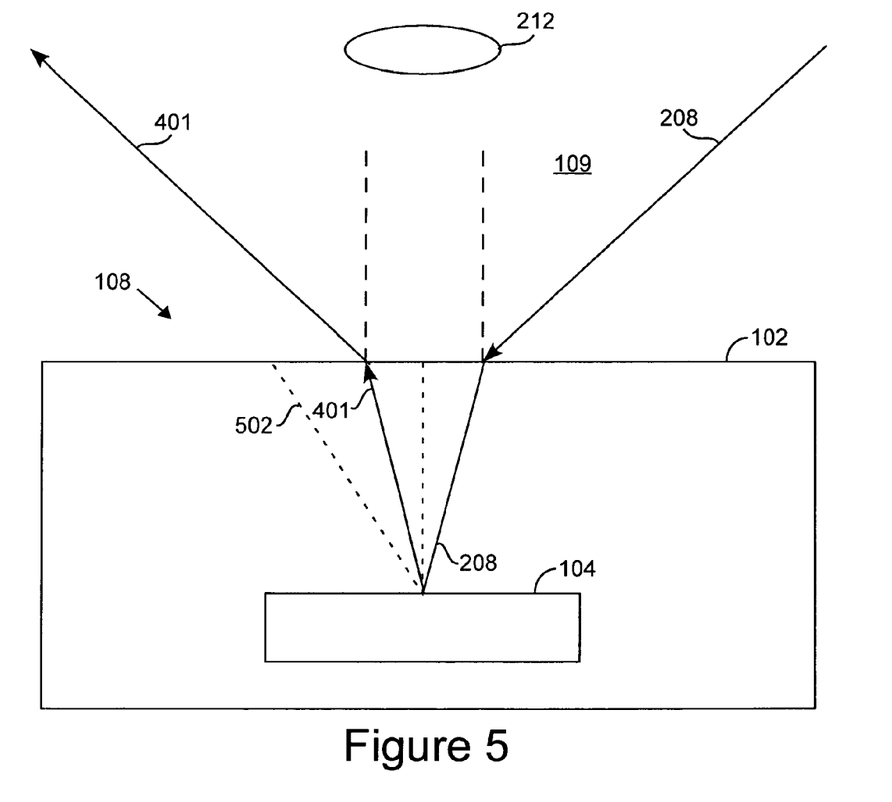
FIG. 5 illustrates one embodiment of the object of FIG. 1 showing a beam reflected off of the surface of a feature of the object over a range of angles.

It can be seen that, as illustrated in FIG. 4, the reflected beam 401 is not incident on the objective 212 within its acceptance angle 306. At least two factors, however, allow portions of the beam 401 to be incident on the objective 212. First, as illustrated in FIG. 3, roughness on the surface 108 of the object 102 may cause the incident beam 208 to actually be incident on the feature 104 over a range of angles, represented by cone 312 shown in FIG. 3. Further, surface roughness of the feature 104 may cause the reflected beam 401 to be scattered over a range 502 of angles, including angles that allow a portion of the reflected beam 401 to be incident on the objective 212 within its acceptance angle (see FIG. 5). It will be appreciated that portions of the beam 401 follow paths similar to those shown in FIG. 4 and, therefore, such portions are not incident on the objective 212. Because a portion of the reflected beam 401 is lost, it may be desirable to choose an illumination source 202 having an intensity relatively greater than what would be used for a similar bright field imaging set-up. For example, in various embodiments, the intensity of the illumination source 202 may be an order of magnitude larger than that used for a similar bright field imaging set-up.

Figure 6:
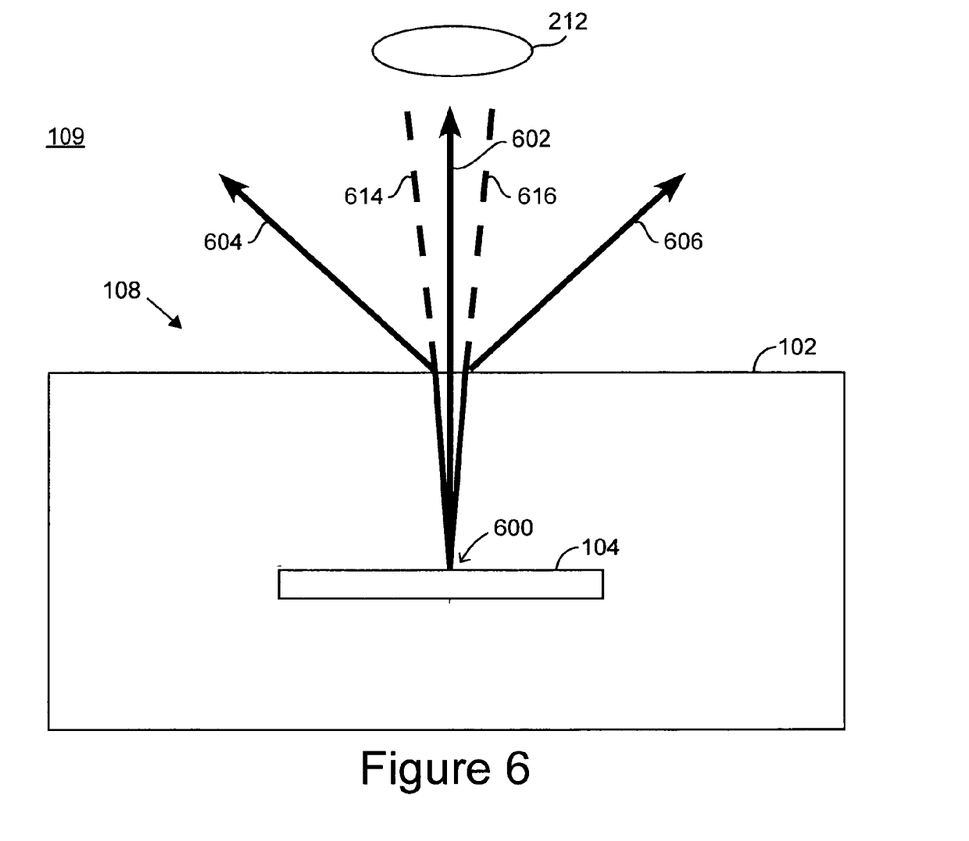
FIG. 6 illustrates one embodiment of the object and feature shown in FIG. 1 showing rays reflected by a point on the feature.

According to various embodiments, refraction at the interface between the surface 108 and the surrounding medium 109 may serve as a spatial filter, increasing the resolution of the image captured by the objective 212 by minimizing the spatial distribution of beams captured from each point of the feature 104. This effect, which can be thought of as an inverse of the Snell's window effect observed under water, is illustrated in FIG. 6. FIG. 6 shows one embodiment of the object 102 and feature 104 including rays 602, 604, 606 reflected by a point 600 on the feature 104. The ray 602 is incident on the surface/surrounding medium 109 interface at an angle within the acceptance range of the objective 212. Accordingly, the ray 602 is received by the objective 212 and transmitted to the imaging device 214 (see FIG. 2). The rays 604 and 606, in contrast, are outside of the acceptance range. As shown by un-refracted paths 614, 616, the rays 604, 606 would ordinarily be incident on objective 212 within its acceptance angle. Because of refraction, however, the rays 604, 606 are bent outside of the acceptance angle of the objective 212. As a result, the minimum spacing between subsurface objects 104 and 106 that can be resolved is based on the wavelength of the incident light 208 divided by the index of refraction of the substrate material 102, thus improving image resolution.

Figure 7:
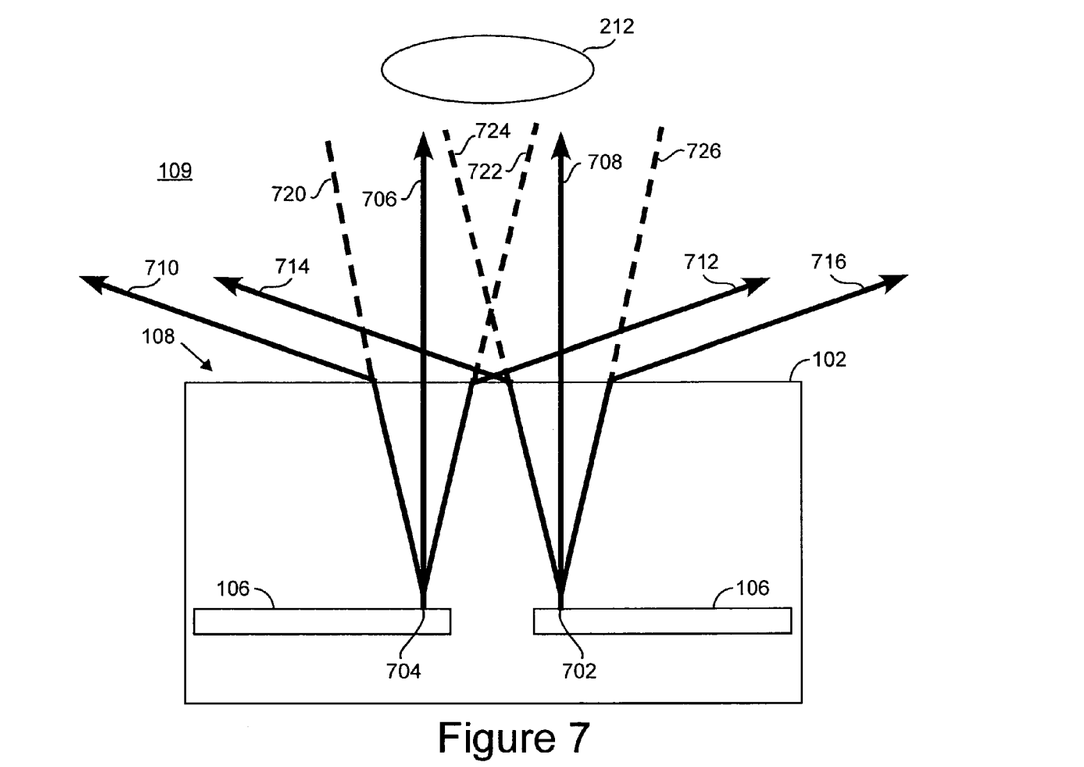

The utility of the spatial filtering effect is demonstrated by FIG. 7, which shows one embodiment of the object 102 showing both of the subsurface features 104, 106. Rays 706, 710 and 712 are reflected off of a point 704 on feature 104. Rays 708, 714 and 716 are reflected off of a point 702 on feature 106. As illustrated, rays 706 and 708 are within the acceptance range and, therefore, are incident on the objective 212. Rays 710, 714, 712 and 716, after refraction at the interface between the object 102 and the surrounding medium 109, are outside of the acceptance range and, therefore, are not incident on the objective 212. Dashed lines 720, 724, 722, 726 indicate the paths of the respective rays 710, 714, 712 absent refraction at the object 102/surrounding medium 109 interface. It will be appreciated that, but for the refraction, ray 714 from point 702 would overlap ray 706 from point 704. This would result in fuzziness and lack of clarity in the resulting image (e.g., in the image, the border between feature 104 and feature 106 would be blurred). As shown, however, the refraction between the object 102 and the surrounding medium 109 minimizes beam overlap from nearby points, thus improving image quality.

Figure 8:
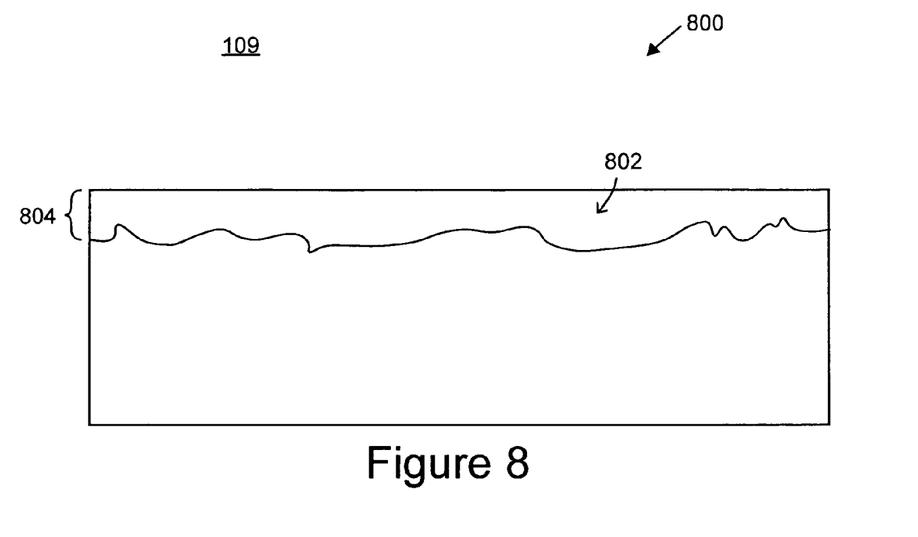
FIG. 8 a cross-sectional view of one embodiment of another object having surface features that may be observed utilizing the side addressed illumination techniques described herein.

Although the figures above are described in the context of backside imaging of semiconductor devices, it will be appreciated that the apparatuses and methods disclosed herein may be used in various other contexts as well. For example, the apparatuses and methods used herein may be used to image any subsurface features where the index of refraction of material between a surface of an object and subsurface features of the object is relatively greater than that of the surrounding medium 109. Also, for example, the apparatuses and methods described herein may be used to image features on the surface of an object by providing a temporary or permanent layer of high refractive index material over the surface prior to imaging. For example, FIG. 8 illustrates a cross-sectional view of one embodiment of another object 800 having surface features 802. The surface features 802 may be imaged by providing a layer 804 of material having a high refractive index at the imaging wavelength range. The layer 804 may be deposited onto the object 800 using any suitable deposition technique. According to various embodiments, the layer 206 may be a fluid, such as an optical coupling fluid, that may be applied to the object 800 in any suitable manner. The layer 206 may be permanent or removable.

It is to be understood that the figures and descriptions of the present invention have been simplified to illustrate elements that are relevant for a clear understanding of the present invention, while eliminating other elements, for purposes of clarity. Those of ordinary skill in the art will recognize that these and other elements may be desirable. However, because such elements are well known in the art and because they do not facilitate a better understanding of the present invention, a discussion of such elements is not provided herein.

In various embodiments disclosed herein, a single component may be replaced by multiple components and multiple components may be replaced by a single component to perform a given function or functions. Except where such substitution would not be operative, such substitution is within the intended scope of the embodiments.

While various embodiments have been described herein, it should be apparent that various modifications, alterations, and adaptations to those embodiments may occur to persons skilled in the art with attainment of at least some of the advantages. The disclosed embodiments are therefore intended to include all such modifications, alterations, and adaptations without departing from the scope of the embodiments as set forth herein.

We claim:

1. A method for generating an image of a surface feature of an object, the method comprising:
    depositing a layer of material over the object, wherein the layer defines an upper surface, and wherein the material has an index of refraction that is greater than an index of refraction of a surrounding medium that surrounds the object and the layer;
    directing illumination in an imaging wavelength range towards the upper surface at a first angle relative to a normal of the upper surface:
        wherein the first angle is greater than an acceptance angle of an objective of an imaging device;
        wherein the material is substantially transparent over the imaging wavelength;
        wherein a first portion of the illumination is reflected at the upper surface and is not incident on the objective;
        wherein a second portion of the illumination is refracted through the upper surface towards the surface feature, is incident on the surface feature and is reflected by the surface feature back towards the upper surface over a range of angles;
        wherein at least an portion of the range of angles is within an acceptance angle of the objective;
        wherein the second portion of the illumination is refracted at the upper surface such that an attenuated component of the second portion is refracted outside of the acceptance angle of the objective and a filtered component of the second portion is incident on the objective.

2. The method of claim 1, further comprising removing the layer of material from the object.

3. The method of claim 1, wherein the material comprises a liquid.

4. The method of claim 3, wherein the material comprises an optical coupling fluid.

5. The method of claim 1, wherein the imaging wavelength range comprises near infrared wavelengths.

6. The method of claim 1, wherein the ratio of the index of refraction of the material over the index of refraction of the surrounding medium is about 3.5.

7. The method of claim 1, wherein the first angle is about 45°.

8. The method of claim 1, wherein the acceptance angle of the objective is about 28°, and wherein the first angle is between 28° and 90° relative to the normal of the upper surface.

9. A system for generating an image of a surface feature of an object through a layer of material deposited over the object, the system comprising:
   an illumination source that directs illumination in an imaging wavelength range toward an upper surface of the layer of material at a first angle relative to a normal of the upper surface; and
   an imaging device defining an objective:
      wherein the first angle is greater than an acceptance angle of the objective;
      wherein the material is substantially transparent over the imaging wavelength range,
      wherein the material has an index of refraction that is greater than an index of refraction of a surrounding medium that surrounds the object and the layer of material;
      wherein a first portion of the illumination is reflected at the upper surface and is not incident on the objective;
      wherein a second portion of the illumination is refracted through the upper surface towards the surface feature, is incident on the surface feature and is reflected by the surface feature back towards the upper surface over a range of angles;
      wherein at least a portion of the range of angles is within an acceptance angle of the objective; and
      wherein the second portion of the illumination is refracted at the upper surface such than an attenuated component of the second portion is refracted outside of the acceptance angle of the objective and a filtered component of the second portion is incident on the objective.

10. The system of claim 9, wherein the material comprises a liquid.

11. The system of claim 10, wherein the material comprises an optical coupling fluid.

12. The system of claim 9, wherein the objective is oriented substantially normal to the upper surface.

13. The system of claim 9, wherein the objective comprises a confocal lens.

14. The system of claim 9, wherein the imaging wavelength range comprises near infrared wavelengths.

15. The system of claim 9, wherein the ratio of the index of refraction of the material over the index of refraction of the surrounding medium is about 3.5.

16. The system of claim 9, wherein the first angle is about 45°.

17. The system of claim 9, wherein the acceptance angle of the objective is about 28°, and wherein the first angle is between 28° and 90° relative to the normal of the upper surface.

* * * * *